United States Patent
Amano et al.

(10) Patent No.: US 7,526,332 B2
(45) Date of Patent: Apr. 28, 2009

(54) METHOD FOR DETERMINING A RIGHT INTENSITY OF FITNESS LEVEL

(75) Inventors: Kazuhiko Amano, Tokyo-To (JP); Hiroaki Tanaka, Fukuoka (JP)

(73) Assignee: Seiko Epson Corporation, Tokyo (JP)

( * ) Notice: Subject to any disclaimer, the term of this patent is extended or adjusted under 35 U.S.C. 154(b) by 313 days.

(21) Appl. No.: 11/428,765

(22) Filed: Jul. 5, 2006

(65) Prior Publication Data

US 2007/0010751 A1 Jan. 11, 2007

Related U.S. Application Data

(60) Provisional application No. 60/696,807, filed on Jul. 7, 2005.

(51) Int. Cl.
*A61B 5/02* (2006.01)
*A61B 5/0255* (2006.01)

(52) U.S. Cl. .................................. 600/513; 600/523

(58) Field of Classification Search ................ 600/500, 600/504, 508, 513, 526, 523
See application file for complete search history.

(56) References Cited

OTHER PUBLICATIONS

Obara, Shigeru, et al. "The First Heart Sound Amplitude Has a Breaking Point and Positive Relationships With Blood Lactate Concentration and Double Product in Graded Exercise," *Adv. Exerc. Sports Physiol.*, vol. 11, No. 1, pp. 33-39, (2005).
Niki, Tetsuya, et al. "Intensification and Breaking Point of Heart Sounds During Graded Exercise," *Adv. Exerc. Sports Physiol.*, vol. 52, No. 6, p. 877, (2003).

*Primary Examiner*—George R Evanisko
*Assistant Examiner*—Rex Holmes
(74) *Attorney, Agent, or Firm*—Oliff & Berridge, PLC (57) ABSTRACT

An aspect of the present invention is related to a method for determining a right intensity for fitness level or exercise stress that includes a first step of inspection a first change of amplitudes of a first heart sound with regard to a second change of intensities of exercise stress, a second step of inspection of a third change of ratios of a first length of a cardiac dilation period relative to a second length of one cardiac cycle with regard to the second change, a third step of identification of a folding point of the first change, and a fourth step of determination of an intensity of the intensities at the folding point as the right intensity of exercise stress if a ratio of the ratios at the intensity is higher than a predetermined value.

7 Claims, 8 Drawing Sheets

METHOD FOR DETERMINING A RIGHT INTENSITY OF FITNESS LEVEL

BACKGROUND OF THE INVENTION

1. Field of Invention

An aspect of the present invention relates to a method to determine a right intensity for one's fitness level based on results of an exercise stress test.

2. Description of Related Art

Several parameters are known to be useful indicators o determine the appropriate exercise intensity in the training or in the ergotherapy, or to evaluate functions of the respiratory organs system and circulatory organ system.

The several parameters includes a threshold level at which the blood lactate concentration begins an upward trend (the conversion from aerobic exercise to anaerobic exercise is considered to occur at the threshold level), the lactate threshold value that is expressed as the numerical value of oxygen uptake, the ventilatory threshold value at which of a sudden increase of the carbon dioxide in the expiration is observed according to the exercise load strength and the anaerobic threshold value.

The above parameters are generally observed or monitored invasively.

On the contrary, a method to determine a right intensity of fitness level or exercise stress based on amplitudes of heart sound has been proposed. Amplitudes of heart sound can be observed or monitored noninvasively.

SUMMARY OF THE INVENTION

An object of an aspect of the present invention is to determine a safe and right intensity of one's fitness level or exercise stress.

A first aspect of the present invention is related to a method for determining a right intensity for fitness level or exercise stress that includes a first step of inspection a first change of amplitudes of a first heart sound with regard to a second change of intensities of exercise stress, a second step of inspection of a third change of ratios of a first length of a cardiac dilation period relative to a second length of one cardiac cycle with regard to the second change, a third step of identification of a folding point of the first change, and a fourth step of determination of an intensity of the intensities at the folding point as the right intensity of exercise stress if a ratio of the ratios at the intensity is higher than a predetermined value.

A second aspect of the present invention is related to a method for determining a right intensity of exercise stress that includes a first step of inspection of a first change of amplitudes of a first heart sound with regard to a second change of intensities of exercise stress, a second step of inspection of a third change of ratios of a first length of a cardiac dilation period relative to a second length of one cardiac cycle with regard to the second change, a third step of identification of a first intensity at a first folding point of the first change a fourth step of identification of a second intensity at a second folding point of the third change, and a fifth step of determination of the second intensity as the right intensity of exercise stress if the second intensity is lower than the first intensity.

A third aspect of the present invention is related to a method for determining a right intensity of exercise stress that includes a first step of inspection of a fourth change of ratios of a first length of a cardiac dilation period relative to a second length of one cardiac cycle with regard to a fifth change of intensities of exercise stress, a second step of identification of a folding point of the fourth change, and a third step of determination of an intensity at the folding point as the right intensity of exercise stress.

The amplitudes of a first heart sound with regard to a second change of intensities of exercise stress changes suddenly in the vicinity of the first folding point.

The of ratios of the first length of a cardiac dilation period relative to the second length of one cardiac cycle changes suddenly in the vicinity of the second folding point.

The first change may be obtained under a resting condition or after an exercise stress in any one of the above methods.

The method may further include a step of evaluation of whether a person being tested is in exercise condition or not by an acceleration sensor.

The acceleration sensor may be attached to a part of a body in any one of the above methods.

The acceleration sensor may be a waist or an arm of the person being tested.

DETAILED DESCRIPTION OF PREFERRED EMBODIMENTS

An exemplified embodiment regarding with the present invention will be explained in reference to drawings below.

Figure 1:
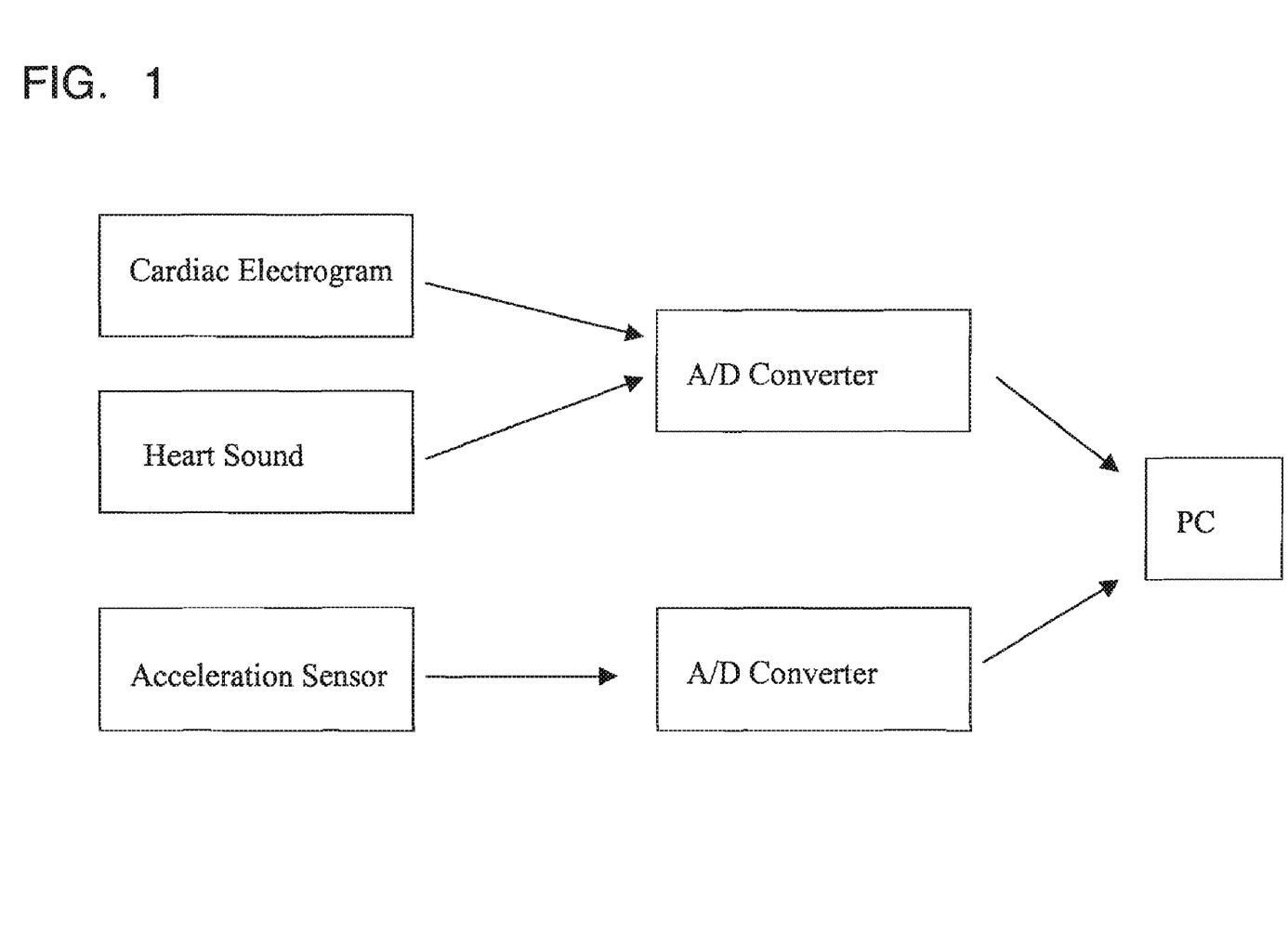
FIG. 1 shows a block diagram for the measuring processing procedure in an exemplified experiment.

FIG. 1 shows a block diagram that shows measuring means employed in the exemplified embodiment.

A cardiac rate is estimated from an electrocardiogram. A cardiac sound is recorded by a microphone attached to a breast. The microphone is covered by a plastic cover having a dome shape. The cardiac sound and the cardiac electronic signal corresponding to a cardiac electrogram were taken in a personal computer through an A/D converter after amplification of the cardiac sound and the cardiac electronic signal.

An output from an acceleration sensor attached to a part of body is taken in a personal computer thorough an A/D converter after amplification of the output.

The acceleration sensor was attached to the lumbar part of a person being tested (23 years old, male, height: 173.5 cm, weight: 70.1 kg) and used for detecting exercise condition of the person being tested.

Figure 2:
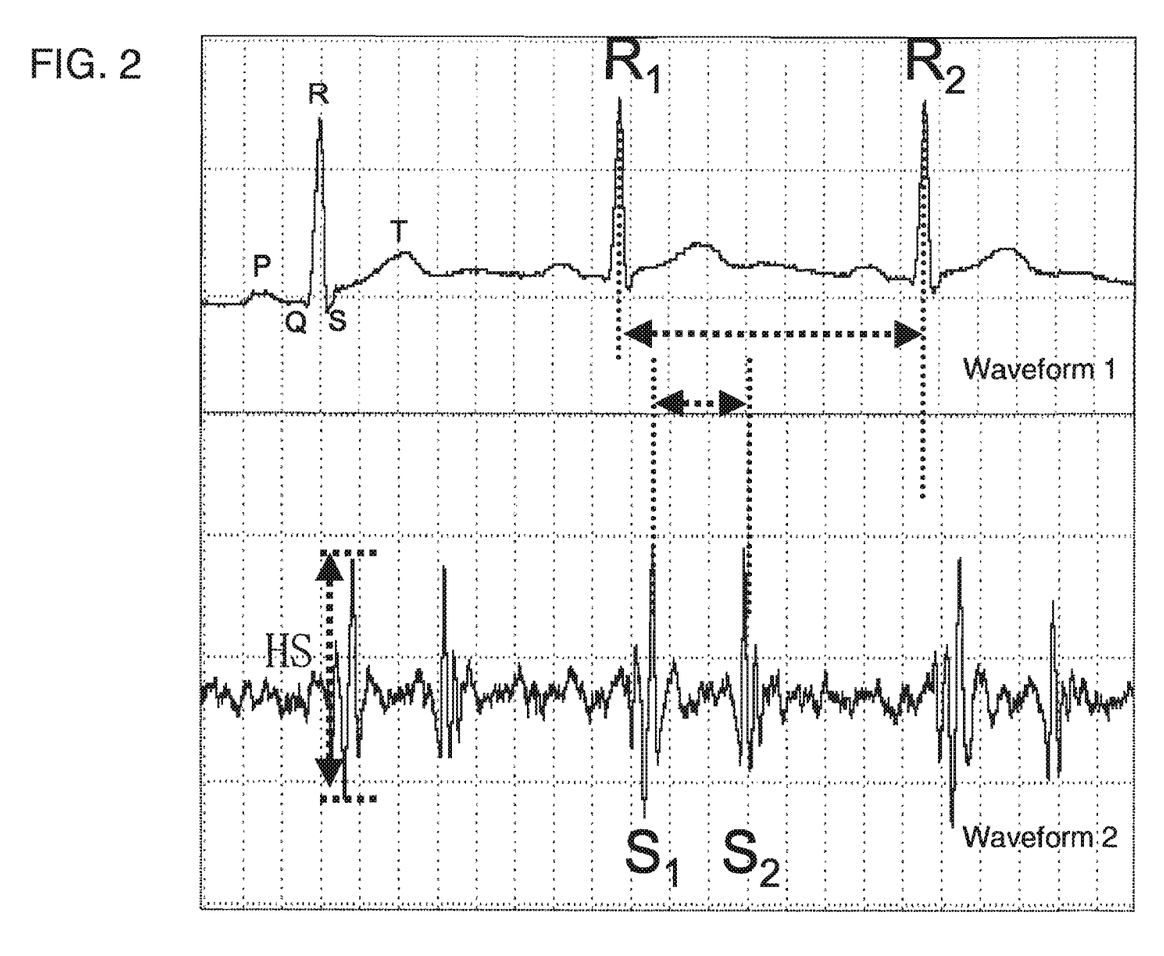
FIG. 2 shows a cardiac electronic signal waveform (waveform 1) and a cardiac sound waveform (waveform 2).

FIG. 2 shows cycles of the person's heart. Waveform 1 and waveform 2 shown in FIG. 2 correspond to a cardiac electrogram waveform and a cardiac sound waveform, respectively.

The period from R1 to R2 corresponds to one cardiac cycle. A first heart sound S1 appears after the appearance of R wave corresponds to a closing sound of mitral valve or eustachian valve, or an opening sound of the aortic valve.

A second heart sound S2 appears after the appearance of T wave corresponds to a closing sound of the aortic valve.

A ratio of a length of a cardiac dilation period relative to a length of one cardiac cycle is estimated by dividing a value obtained by subtracting the length of the period from S2 to S1 from the length of the period from R1 to R2 by the length of the period from R1 to R2.

The heart may become ischemic if the ratio of the length of the cardiac dilation period relative to the length of one cardiac cycle is extremely low because oxygen is supplied to myocardium during the cardiac dilation period. The ratio should be higher than 50% for narrowing of coronary arteries for safety's sake.

Figure 3:
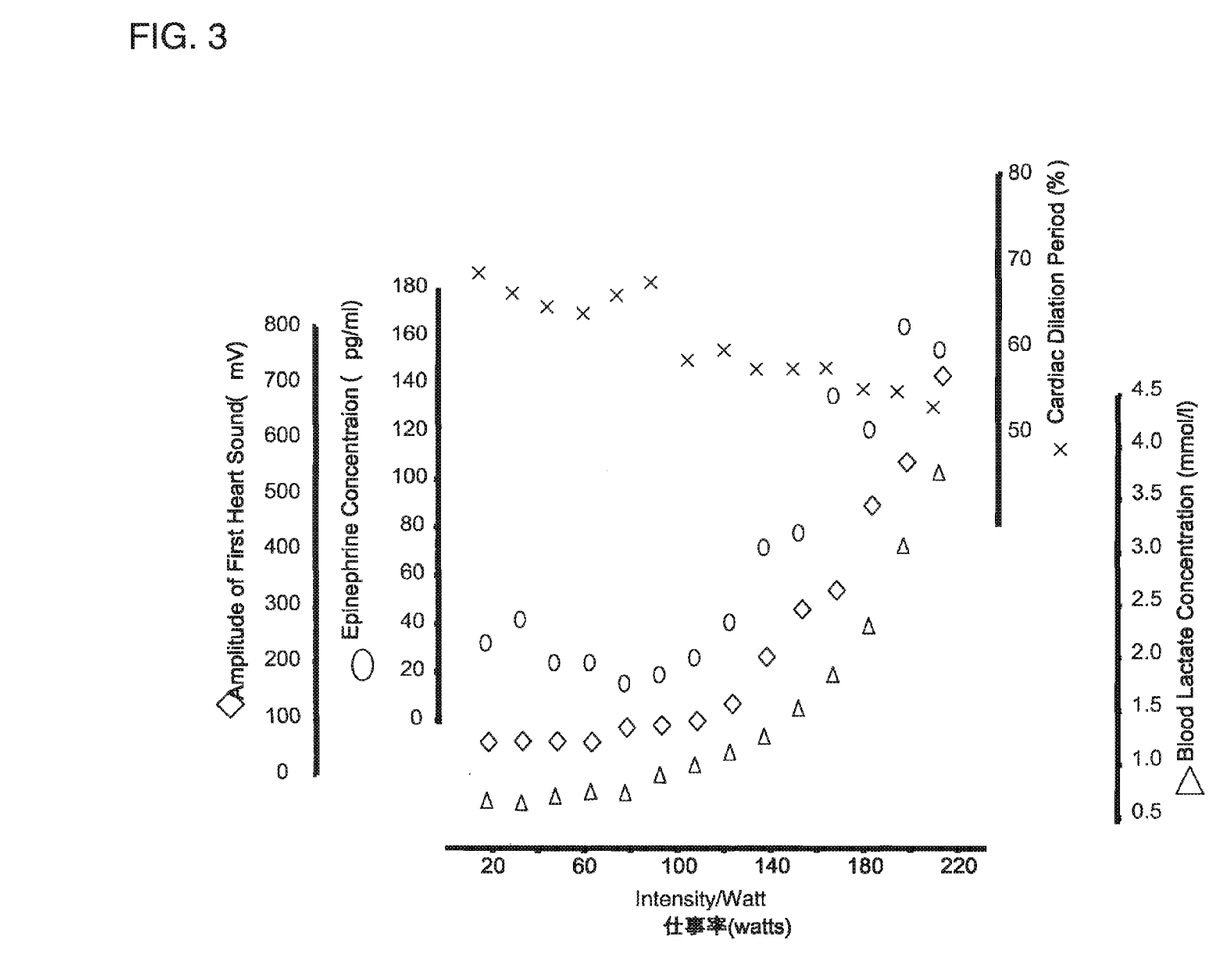
FIG. 3 shows changes of amplitude of first heart sound S1 (mV), ratio of a length of a cardiac dilation period relative to a length of one cardiac cycle (%), epinephrine concentration (pg/ml) and blood lactate concentration (mmol/l) according to change of intensity of an exercise stress after 10 times of heart beats from the end of the exercise stress.

FIG. 3 shows changes of amplitude of first heart sound S1 (mV), ratio of a length of cardiac dilation period relative to a length of one cardiac cycle (%), epinephrine concentration (pg/ml) and blood lactate concentration (mmol/l) according to change of exercise stress intensity after 10 times of heart beats from the end of the exercise.

HSBP (Heart Sound Break Point) where the amplitude of the first cardiac sound changes sharply appears at around 120 watt clearly.

Epinephrine concentration begins an upward trend in the vicinity of the HSBP.

Blood lactate concentration begins also an upward trend in the vicinity of the HSBP.

It is can be concluded that change of the amplitude of first cardiac sound according to change of load strength of the exercise or intensity of the exercise stress correlates with changes of epinephrine concentration and blood lactate concentration according to change of load strength of the exercise or intensity of the exercise stress.

This indicates that a right intensity of fitness level or exercise stress can be determined by examining change of the amplitude of the first cardiac sound, which can be observed noninvasively.

As mentioned above, it is possible to determine a right intensity of fitness level or exercise stress based on change of amplitude of first cardiac sound.

It is preferable to consider length of cardiac dilation period to assure safeness in addition to change of amplitude of the first cardiac sound.

If a criterion ratio of the length of cardiac dilation period relative to the length of period of one cardiac cycle below which is contraindicated with a patient is known in advance, it is possible to determine a safe and right fitness level of patient based on the criterion ratio.

For example, it is preferable to confirm that the criterion ratio of the length of cardiac dilation period relative to the length of the period of one cardiac cycle is higher than 50% at a right intensity of exercise stress estimated from amplitude of first cardiac sound because this may cause ischemia of a patient with a symptom such as narrowing of coronary arteries if the ratio of length of cardiac dilation period relative to length of period of one cardiac cycle is 50% or less.

In the exemplified embodiment, a right intensity of exercise stress estimated from amplitude of first cardiac sound may be safe because a ratio of the length of cardiac dilation period relative to length of period of one cardiac cycle at (HSBP) is higher than 50%.

It is desirable to pay attention to a folding point of the change of the ratio of the length of cardiac dilation period relative to the length of the period of one cardiac cycle to determine an safe exercise strength.

As shown in FIG. 3, the change of the ratio of length of cardiac dilation period relative to length of period of one cardiac cycle has a folding point ranging from 80 watt to 90 watt where a sharp change is observed. The folding, point corresponds to change of cardiac burden.

It is preferable to determine intensities between 80 watt and 90 watt as a right intensity for a severe patient. A right intensity of exercise stress for the severe patient can be estimated from a folding point of the change of ratio of the length of cardiac dilation period relative to length of the period of one cardiac cycle.

Changes of amplitude of first heat sound and ratio of length of cardiac dilation period relative to length of the period of one cardiac cycle are useful indicators to determine a safe and appropriate intensity of exercise stress.

If an intensity corresponding to a folding point of change of ratio of the length of cardiac dilation period relative to the length of the period of one cardiac cycle is lower than an intensity corresponding to folding point of change of amplitude of the first heat sound, a right intensity of exercise stress can be easily determined only based on change of ratio of length of cardiac dilation period relative to length of period of one cardiac cycle.

Figure 4:
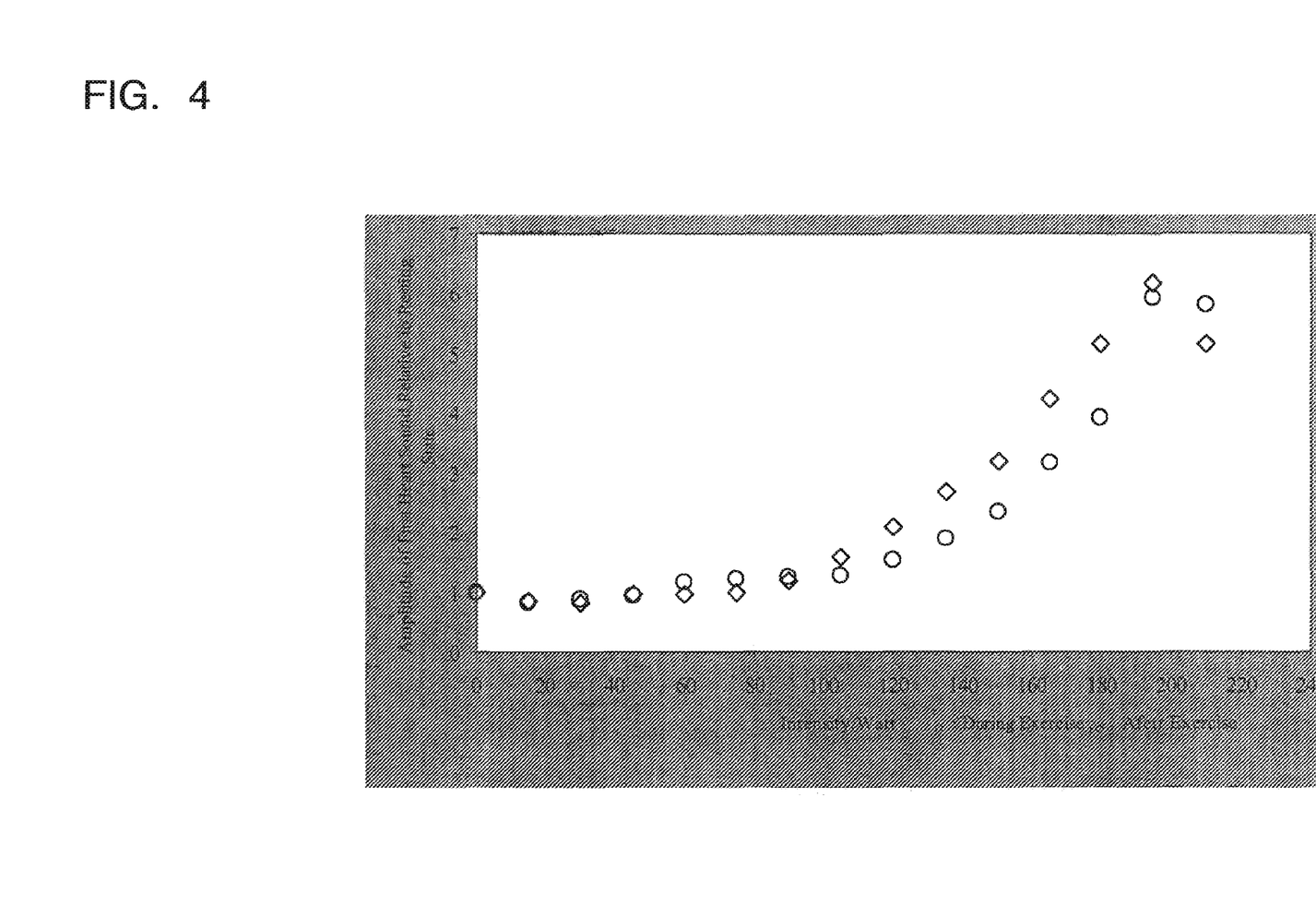
FIG. 4 shows a comparison between a change of amplitude of the first heart sound during exercise and a change of amplitude of the first heart sound after exercise.
Figure 5:
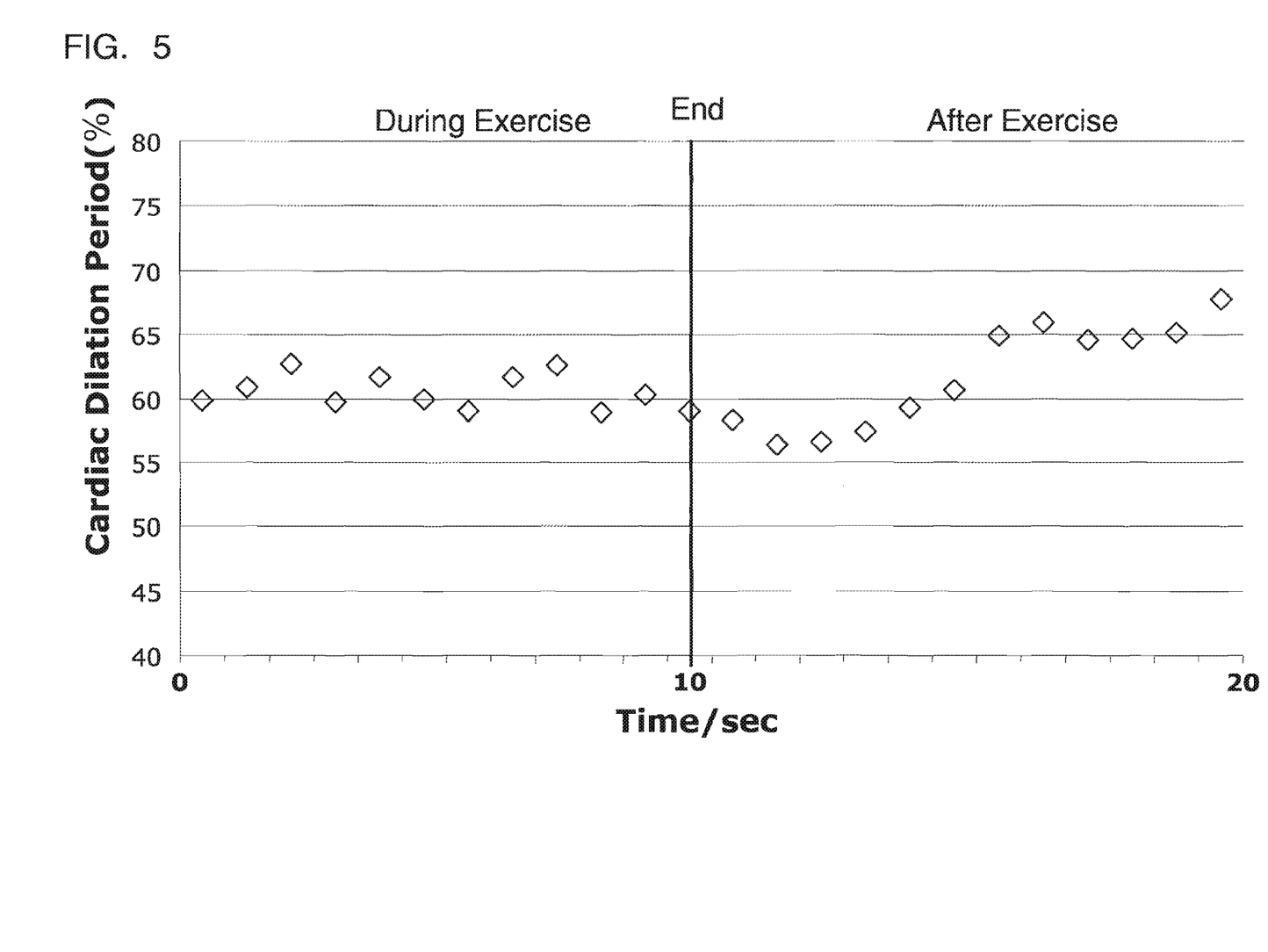
FIG. 5 shows changes of ratio of a length of a cardiac dilation period relative to a length of one cardiac cycle for 10 seconds before and after the end of exercise stress whose intensity is 50 watt.
Figure 6:
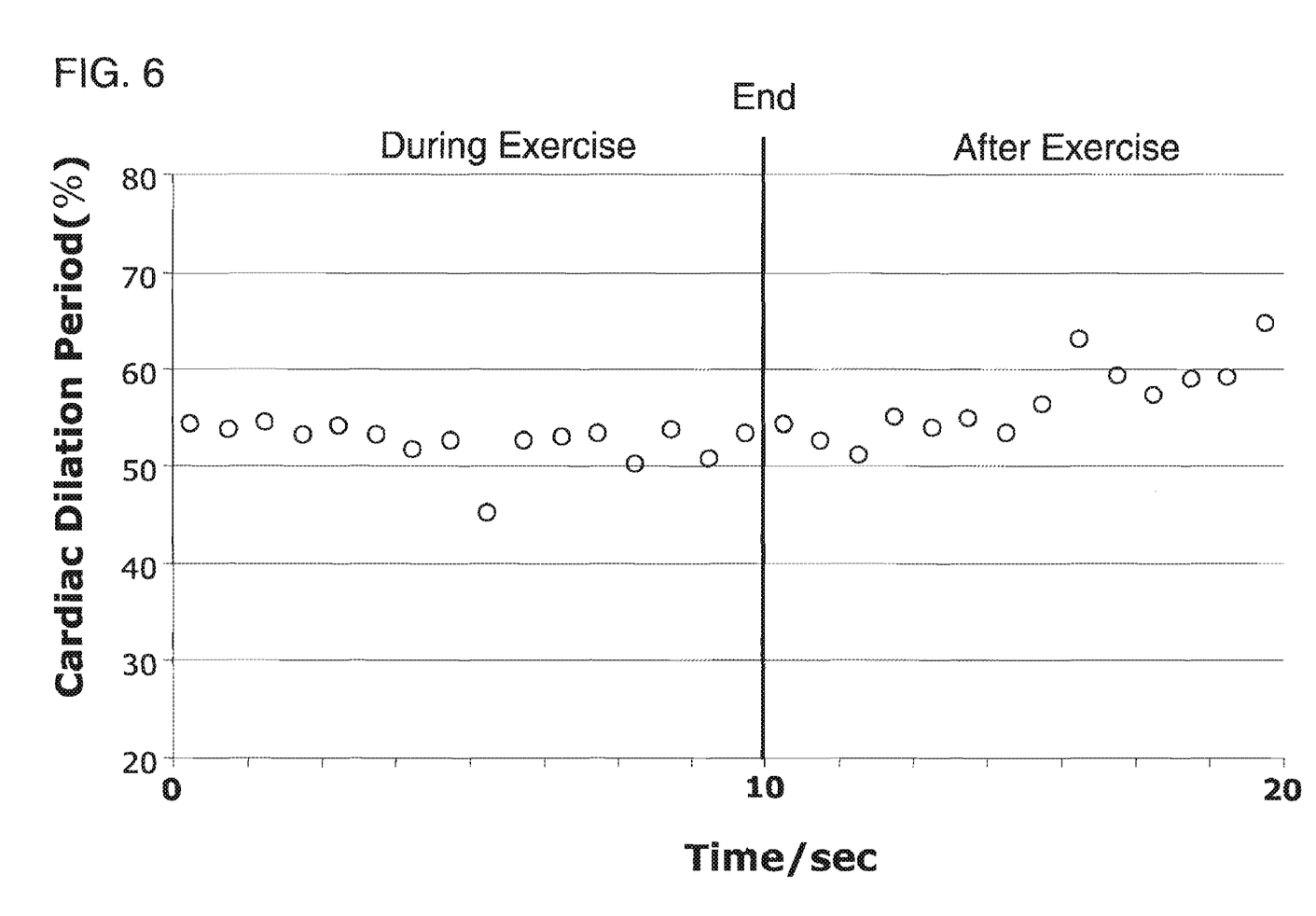
FIG. 6 shows changes of ratio of a length of a cardiac dilation period relative to a length of one cardiac cycle for 10 seconds before and after the end of exercise stress whose intensity is 100 watt.
Figure 7:
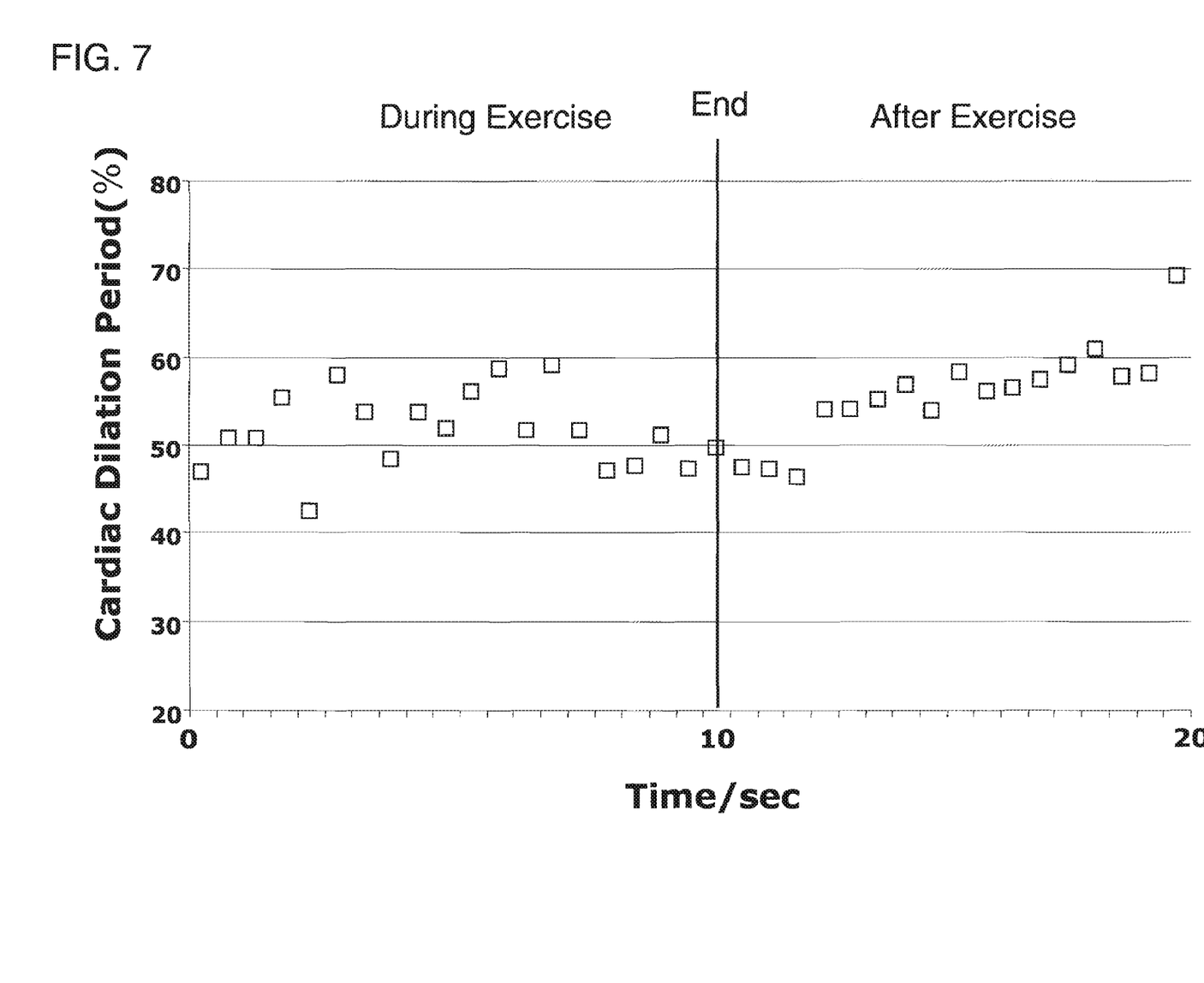
FIG. 7 shows changes of ratio of a length of a cardiac dilation period relative to a length of one cardiac cycle for 10 seconds before and after the end of exercise stress whose intensity is 150 watt.
Figure 8:
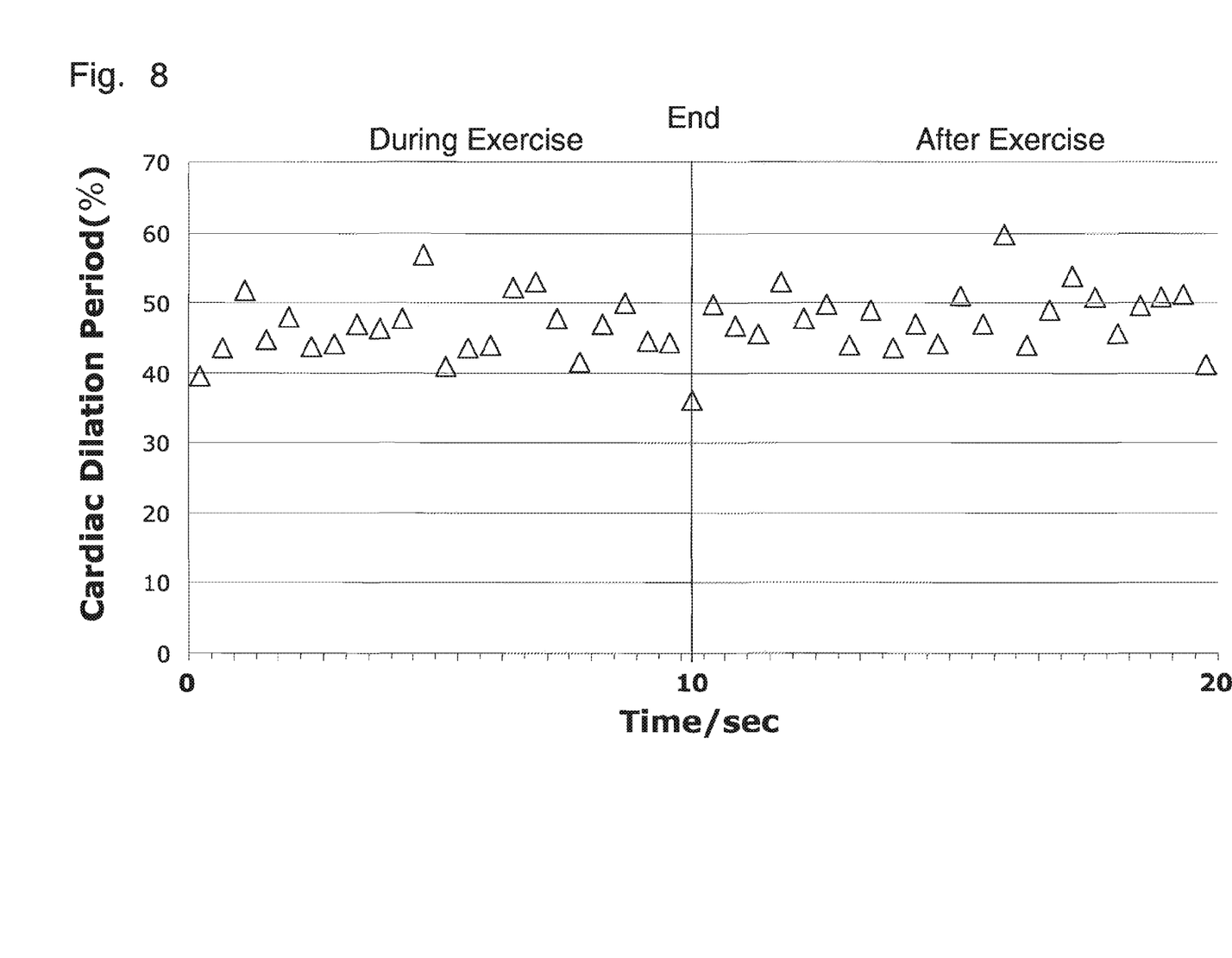
FIG. 8 shows changes of ratio of a length of a cardiac dilation period relative to a length of one cardiac cycle for 10 seconds before and after the end of exercise stress whose intensity is 200 watt.

FIG. 4 shows a comparison between a change of amplitude of the first heart sound during exercise and change of amplitude of first heart sound after exercise.

Change of amplitude of first heart sound during exercise was obtained by averaging amplitudes of first heart sound detected with almost no noise during 30 seconds before the end of an ergometer exercise.

Change of amplitude of first heart sound after exercise was obtained by averaging amplitudes of first heart sound detected during ten times of heart beats just after the ergometer exercise.

A folding point obtained from amplitude of first heart sound after exercise appears more clearly than a folding point obtained from amplitude of first heart sound during exercise as shown in FIG. 4.

It is possible to easily determine an appropriate intensity of exercise stress by inspecting amplitudes of the first heat sound just after exercise.

As mentioned above, it is preferable to inspect amplitudes of first heat sound just after exercise to determine an appropriate intensity of exercise stress.

An acceleration sensor can be used for inspection of exercise condition. The acceleration sensor may be attached a body of a person being tested.

An acceleration sensor may be attached to a pectoral region. In this case, the acceleration sensor may be used as a microphone for detecting heat sounds.

An acceleration sensor may be attached to a part of body to which a microphone is attached.

It is necessary to inspect change of ratio of length of cardiac dilation period relative to length of period of one cardiac cycle during exercise to determine a right intensity of exercise stress exactly. However, it is difficult because of noise generated during exercise.

However, As shown in FIGS. form 5 to 8, there is little difference between change of ratio of length of cardiac dilation period relative to length of period of one cardiac cycle during exercise and change of ratio of length of cardiac dilation period relative to length of period of one cardiac cycle during 10 seconds just after the end that exercise.

Therefore, it is proper to determine a right intensity of exercise stress based on change of ratio of length of cardiac dilation period relative to length of period of one cardiac cycle during a short period just after the exercise.

If a criterion ratio of length of cardiac dilation period relative to length of period of one cardiac cycle is set to be higher than 50%, a ratio of length of cardiac dilation period relative to length of the period of one cardiac cycle for 50 watt of intensity of exercise stress and a ratio of length of cardiac dilation period relative to length of the period of one cardiac cycle for 50 watt of intensity of exercise stress are higher than 50% together.

Accordingly, a right intensity of exercise stress can be considered to be in the range from 50 watt to 100 watt. This correlates with that the folding point of change of ratio of length of cardiac dilation period relative to length of the period of one cardiac cycle as described above.

What is claimed is:

1. A method for determining a right intensity of exercise stress, comprising the following computer implemented steps:
    inspecting a first change of amplitudes of a first heart sound corresponding to a second change of intensities of exercise stress;
    inspecting a third change of ratios of a first length of a cardiac dilation period relative to a second length of one cardiac cycle corresponding to the second change;
    identifying a folding point of the first change; and
    determining an intensity of the intensities of exercise stress at the folding point as the right intensity of exercise stress if a ratio of the ratios at the intensity is higher than a predetermined value.

2. A method for determining a right intensity of exercise stress, comprising the following computer implemented steps:
    inspecting a first change of amplitudes of a first heart sound corresponding to a second change of intensities of exercise stress;
    inspecting a third change of ratios of a first length of a cardiac dilation period relative to a second length of one cardiac cycle corresponding to the second change;
    identifying a first intensity at a first folding point of the first change;
    identifying a second intensity at a second folding point of the third change;
    determining the second intensity as the right intensity for exercise stress if the second intensity is lower than the first intensity.

3. The method according to claim 2, further comprising:
    inspecting a fourth change of ratios of a first length of a cardiac dilation period relative to a length of one cardiac cycle corresponding to a fifth change of intensities of exercise stress;
    identifying a folding point of the fourth change; and
    determining an intensity at the folding point as the right intensity of exercise stress.

4. The method according to claim 1, further comprising:
    obtaining the first change when a body is under a resting condition or after an exercise stress.

5. The method according to claim 1, further comprising:
    using output from an acceleration sensor attached to a body to evaluate whether the body is under an exercise condition.

6. The method according to claim 5, wherein the acceleration sensor is attached to a part of the body.

7. The method according to claim 6, wherein the acceleration sensor is attached to a waist or an arm of the body.

* * * * *